(12) United States Patent
Ando et al.

(10) Patent No.: US 7,732,791 B2
(45) Date of Patent: Jun. 8, 2010

(54) SEMICONDUCTOR TESTING METHOD AND SEMICONDUCTOR TESTER

(75) Inventors: Tohru Ando, Tokyo (JP); Yasuhiko Nara, Hitachinaka (JP); Tsutomu Saito, Hitachinaka (JP); Shinichi Kato, Mito (JP); Takeshi Sunaoshi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 222 days.

(21) Appl. No.: 11/834,207

(22) Filed: Aug. 6, 2007

(65) Prior Publication Data

US 2008/0237462 A1 Oct. 2, 2008

(30) Foreign Application Priority Data

Sep. 4, 2006 (JP) .............................. 2006-238757

(51) Int. Cl.
*H01J 49/00* (2006.01)
*G06K 9/00* (2006.01)
*G06K 9/62* (2006.01)

(52) U.S. Cl. .............................. 250/492.22; 250/492.1; 250/492.23; 324/751; 324/752; 382/145; 382/149

(58) Field of Classification Search ........................ None
See application file for complete search history.

(56) References Cited

U.S. PATENT DOCUMENTS

| 6,723,973 | B2 * | 4/2004 | Saito ..................... 250/492.22 |
| 6,734,687 | B1 * | 5/2004 | Ishitani et al. .............. 324/751 |
| 6,772,089 | B2 * | 8/2004 | Ikeda et al. .................. 702/159 |
| 6,970,004 | B2 * | 11/2005 | Ishitani et al. .............. 324/752 |
| 7,321,680 | B2 * | 1/2008 | Ikeda et al. .................. 382/145 |
| 7,397,178 | B2 * | 7/2008 | Ito et al. ..................... 313/504 |
| 7,524,689 | B2 * | 4/2009 | Kato et al. .................... 438/30 |
| 2004/0178811 | A1 * | 9/2004 | Ishitani et al. .............. 324/751 |
| 2007/0047800 | A1 * | 3/2007 | Hiroi et al. .................. 382/149 |

FOREIGN PATENT DOCUMENTS

JP 2000-251824 A 9/2000

* cited by examiner

*Primary Examiner*—David A Vanore
(74) *Attorney, Agent, or Firm*—Crowell & Moring LLP

(57) ABSTRACT

A semiconductor testing method capable of quickly counting semiconductor cells in which a seemingly horizontal or vertical line is drawn with a mouse, and raster rotation is performed in alignment with the closer axis. After that, the stage is horizontally moved, pattern matching is performed on an image on a position where the image should be disposed, and an angle is adjusted. The stage is moved evenly along the X-axis and the Y-axis, achieving a movement to a destination like a straight line. In synchronization with the smooth movement of the stage, a cell is surrounded in a rectangular frame by a ruler, and the number of cells is displayed with a numeric value.

19 Claims, 10 Drawing Sheets

SEMICONDUCTOR TESTING METHOD AND SEMICONDUCTOR TESTER

BACKGROUND OF THE INVENTION

1. Field of the Invention

The present invention relates to a semiconductor testing method and a semiconductor tester for testing a semiconductor or conducting a failure analysis with the function of a scanning electron microscope (SEM).

2. Background Art

As failure analyses conducted on semiconductors having basic patterns regularly disposed in a repeated manner, failure analyses are conducted on semiconductors through images obtained by scanning electron microscopes (SEMs) and focused ion beams (FIBs).

In recent years, semiconductor miniaturization has proceeded to 45/65 nm, which is a level higher than the accuracies of stopping stages. Thus it has become difficult to locate a failure even with high-powered microscopes. Further, some failures cannot be recognized at all from the appearances even through observation using SEM images. To be specific, such failures cannot be recognized until probes are brought into contact with the points of failures to measure device characteristics.

In this case, it is necessary to accurately count the positions of failures among completely identical basic patterns disposed in a repeated manner. This is because it is completely meaningless to measure the electrical characteristics of a cell adjacent to the position of a failure.

Particularly, examples of a method of accurately counting failed cells having repeatedly disposed basic patterns include, as described in JP Patent Publication (Kokai) No. 2000-251824A, a pattern matching method, a method of reaching a location of measurement from absolute distance information about a stage, and a method of counting failed cells while moving a stage.

Since pattern recognition is used in the pattern matching method of the conventional art, it is necessary to divide, before recognition, a distance to a destination into units enabling image recognition. Further, since it is desired to keep the movement of a stage as long as possible, the maximum distance enabling image recognition is equivalent to one screen. Since a correction is made for each screen, when a specific cell A in a screen is moved with a stage substantially by one screen, the cell A may be placed out of a specific region for pattern matching due to semiconductor miniaturization. Further, the initial speed and stopping speed of the stage become unstable during the movement. Moreover, the stage is stopped for each screen, causing a drawback of a low speed in view of performance.

In other words, due to semiconductor miniaturization, the accuracy of stopping the stage may cause an error equal to or larger than a spacing between cells relative to the movement of the stage for each screen, so that the cells may be erroneously detected. Although it is convenient to count cells both in rows and columns at the same time, the stage simultaneously moves in both directions and thus an erroneously recognized adjacent cell cannot be visually confirmed. Therefore, such counting is hard to realize.

Further, in the method of reaching a location of measurement based on absolute distance information about a stage according to the conventional art, the position of a failure is calculated from a design drawing by using a CADNavi system and the like, and then the stage is moved. In this method, the accuracy of stopping the stage is larger than the spacing between cells and thus a failure cannot be accurately located.

As a matter of course, it is preferable that the stage can be stopped with high accuracy and can be correctly moved. In either case, a failure has to be accurately located.

Further, in the method of counting cells while moving a stage according to the conventional art, several hundreds of thousands of counts are simply necessary. Such counting is practically impossible.

An object of the present invention is to realize a semiconductor testing method and a semiconductor tester which can quickly and accurately count semiconductor cells.

SUMMARY OF THE INVENTION

According to a semiconductor testing method of the present invention, a plurality of cells formed in a semiconductor are displayed on display means based on a sample signal obtained by irradiating the semiconductor on a movable stage with a charged particle beam, and a specific cell is identified.

The semiconductor testing method of the present invention, comprising the steps of: displaying a rectangular frame surrounding each of the cells displayed on the display means and formed in the semiconductor and displaying a numeric value corresponding to the cell in the displayed rectangular frame; displaying the rectangular frame and the numeric value and simultaneously moving the stage to move the semiconductor based on the sample signal obtained from the semiconductor; and correcting an amount of error, counting the cells, and identifying the specific cell while confirming the numeric value corresponding to the cell.

A semiconductor tester of the present invention comprises a movable stage for supporting a semiconductor, a charged particle beam irradiation optical system for irradiating the semiconductor on the stage with a charged particle beam, a monitor for displaying, based on a sample signal obtained by irradiating the semiconductor with the charged particle beam, a plurality of cells formed in the semiconductor, and a control unit for controlling the stage, the charged particle beam irradiation optical system, and the monitor.

The control unit of the semiconductor tester of the present invention displays a rectangular frame surrounding each of the cells displayed on the monitor and formed in the semiconductor, displays a numeric value corresponding to the cell in the displayed rectangular frame, displaying the rectangular frame and the numeric value and simultaneously moving the stage to move the semiconductor based on the sample signal obtained from the semiconductor.

According to the present invention, it is possible to achieve a semiconductor testing method, a semiconductor tester, and a computer program of the semiconductor tester which can quickly count semiconductor cells with accuracy, thereby improving usability for a user of the tester.

DETAILED DESCRIPTION OF THE PREFERRED EMBODIMENTS

An exemplary embodiment of the present invention will now be described with reference to the accompanying drawing.

Figure 1:
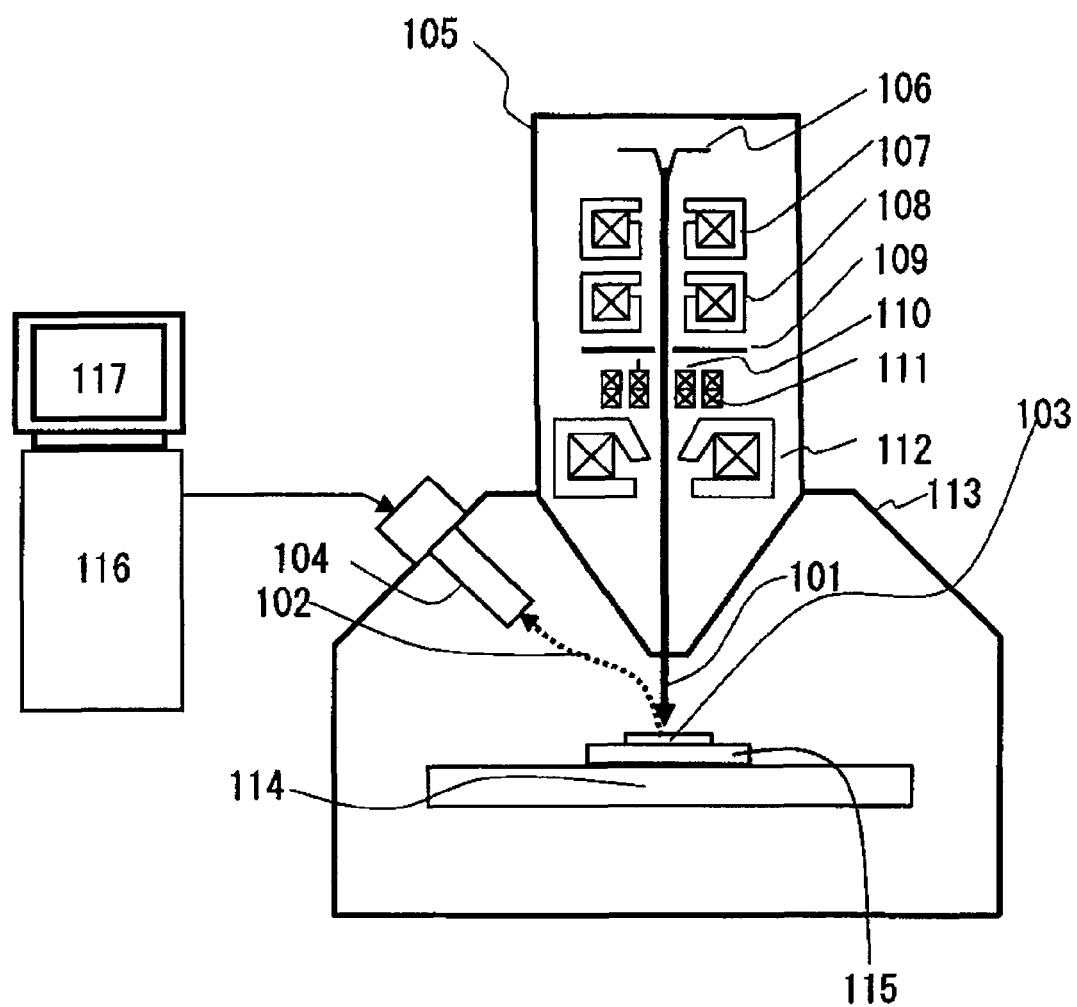
FIG. 1 is a structural diagram schematically showing a semiconductor tester to which an embodiment of the present invention is applied.

FIG. 1 is a structural diagram schematically showing a semiconductor tester to which the embodiment of the present invention is applied.

In FIG. 1, the semiconductor tester emits a primary electron beam 101 including a SEM (Scanning Electron Microscope) beam and an FIB (Focused Ion Beam) to a sample 103 shaped like a thin piece in a vacuum chamber diaphragm 113. Further, a secondary electron beam 102 is detected by a secondary electron detector 104 and an image of a semiconductor is displayed on a display 117 through a control computer 116. The control computer 116 controls the operations of the overall semiconductor tester and also controls the operations of a cell counter (described later) according to a computer program.

An electron beam irradiation optical system 105 generates the primary electron beam 101 from an electron gun 106 through condenser lenses 107 and 108, a diaphragm 109, a scan polariscope 110, an image shift polariscope 111, and an object lens 112. In order to move the sample 103 on a stage pedestal 115 to a desired test position, a stage 114 has moving means of the X-axis and the Y-axis and moving means of the Z-axis (height direction) for focusing.

The stage 114 does not have any mechanisms for rotating the sample 103. In order to rotate the sample 103, an image is rotated by a raster rotation using the scan polariscope 110.

In the embodiment of the present invention, an image shift is used for correction and so on. The image is shift is used such that the position of a field of view is moved by bending the electron beam 101 through the image shift polariscope 111 without moving the stage 114. Most of algorithms constructed in the embodiment of the present invention are implemented by the control computer 116 and some of the algorithms for stage control and the like are implemented by a microcomputer.

Figure 2:
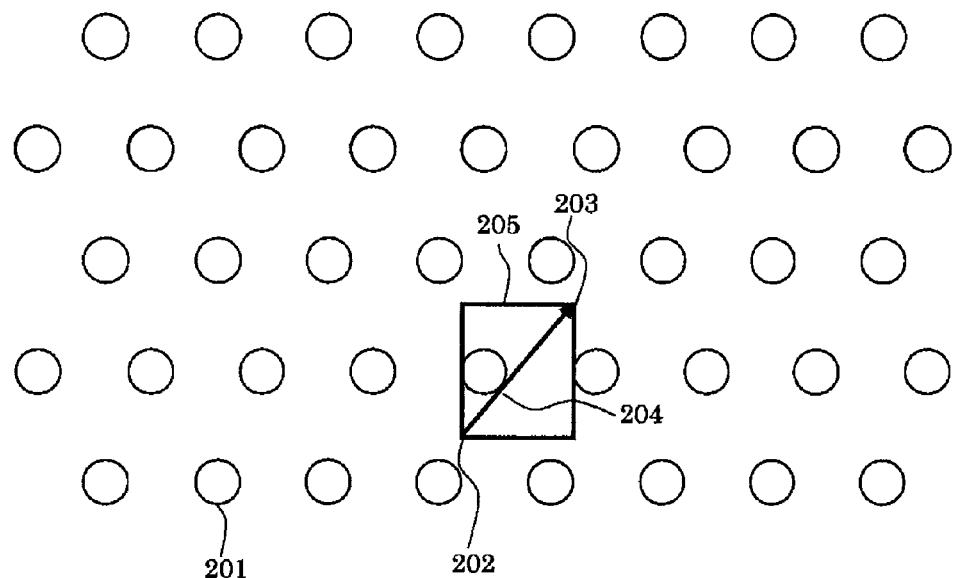
FIG. 2 shows a cell counter initial display operation diagram according to the embodiment of the present invention.

FIG. 2 shows a cell counter initial display operation diagram for an operator according to the embodiment of the present invention. FIG. 2 also shows cells referred through a scanning electron microscope (SEM). It is assumed that a movement to a mat to be measured is made through CADNavi and the like because it takes a long time to count all the cells. Therefore, several thousands cells can be counted at the maximum.

In FIG. 2, a plurality of cells 201 disposed over a screen have patterns regularly disposed in a repeated manner. The patterns cannot be distinguished at all from those of other cells 201 from the appearances. A vector 204 of a unit pattern designated by a user (operator) has a starting point 202 and an end point 203. FIG. 2 shows a rectangle 205 having the vector 204 as a diagonal line.

Figure 3:
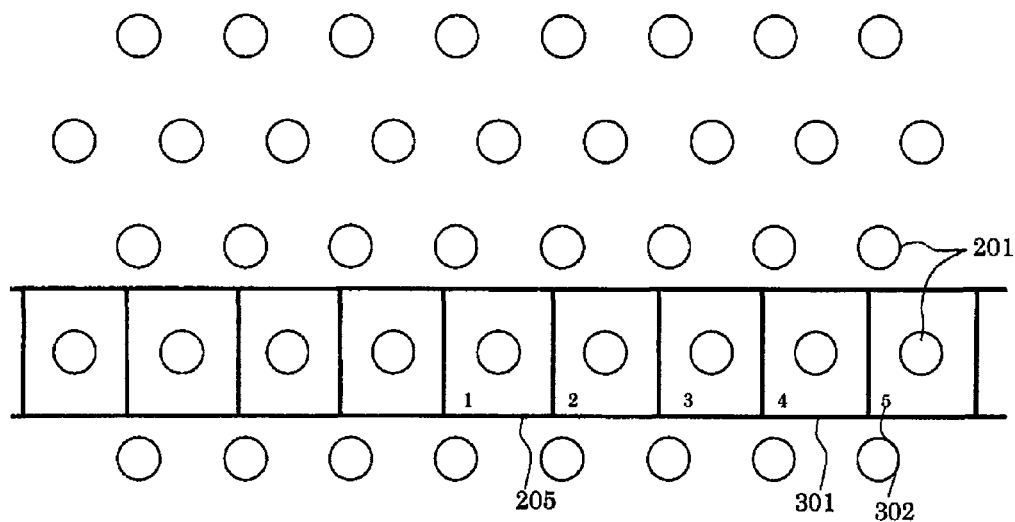
FIG. 3 is an operation diagram of the cell counter according to the embodiment of the present invention.

FIG. 3 shows that a cell counter according to the embodiment of the present invention is displayed with the cells 201 referred through the scanning electron microscope (SEM).

In FIG. 3, a ruler 301 has the rectangular frames 205 consecutively formed to surround the unit patterns 201 and the number of consecutive unit patterns is displayed as a numeric value 302.

After clicking a cell count start button (not shown) on a display and the like, the user performs the following operations:

In FIGS. 2 and 3, after pressing the cell count start button, the user clicks the starting point 202 of the vector of the unit pattern 201 with a mouse and drags the mouse to the end point 203 of the vector of the unit pattern 201, so that the rectangular frame 205 including the vector 204 of the unit pattern and the unit pattern is displayed.

When releasing the mouse at a correct size of the rectangle (dragging is completed), the vector 204 of the unit pattern 201 is erased and the rectangular frames 205 displayable on the screen and the numeric value 302 corresponding to the number of the rectangular frames 205 are displayed.

The rectangular frame 205 is enlarged or reduced laterally with the click of the left mouse button and longitudinally with the click of the right mouse button. The numeric value 302 is oriented as the frame component of the vector of the unit pattern 201. Further, the orientation of the frame 205 and the orientation of the numeric value 302 can be corrected also by a selection through a radio button on another screen.

After a correction button displayed on the screen is pressed, the rectangular frame 205 can be corrected as follows: the inside of the frame 205 is selected with the mouse to move the entire frame 205, a corner of the frame 205 is selected with the mouse to resize the frame 205, or the numeric value 302 is clicked with the mouse to reset the numeric value. Although this operation is performed to the right along the X-axis in this example, operations along the Y-axis and to the left along the X-axis can be also represented as the click of the right mouse button and the positions of the starting point and the end point of the vector.

In the conventional art, operations are performed simultaneously along the X-axis and the Y-axis to count cells in a two-dimensional manner, whereas in the embodiment of the present invention, cells are counted in a one-dimensional manner because few errors occur when cell counting is confirmed along one of the axes.

In the present invention, two-dimensional counting can be achieved by counting cells twice in the X direction and the Y direction.

When the frame 205 is displayed at the center of the cell 201 at a time, a spacing between the cells 201 and a spacing of the frames are not equal to each other. Thus in order to correctly display the frames 205, the following operations are performed.

As shown in FIG. 2, the vector 204 is displayed from the left end of one cell 201 to the left end of the subsequent cell 201, and then one of the frames of the vector 204 is dragged. Thus the center of the frame 205 is moved to the center of the cell 201, so that the spacing between the cells and the spacing between the frames can be correctly aligned with each other to display the cell at the center of the frame. As a matter of course, instead of fixing the left end of the cell 201, alignment on the right end or at the center of the cell 201 is also acceptable.

Moreover, when the plurality of cells 201 are displayed in one frame 205, a plurality of identical cell patterns are present in the one frame 205. Thus there is a high probability of erroneous recognition during correction through image pattern recognition. Further, when the rectangular frame 205 has a mat end, the cell pattern of the rectangular frame 205 may be different from that of the subsequent rectangular frame 205. Thus it is important that only one cell is stored in one rectangular frame.

The initial display of cell counting in the displayed screen is completed thus.

The velocity of the stage will be described below before the description of cell counting.

Figure 4:
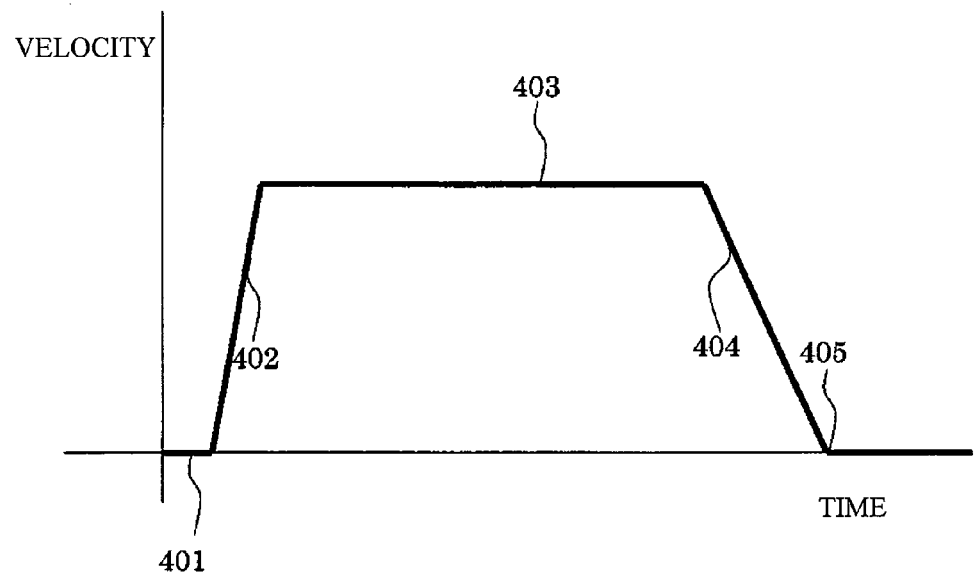
FIG. 4 is a graph showing the relationship between the moving velocity of a stage and a time.

FIG. 4 is a graph showing the relationship between the moving velocity of the stage 114 and a time. In FIG. 4, reference numeral 401 denotes a velocity during backlash, reference numeral 402 denotes the initial movement of the stage 114, reference numeral 403 denotes a stable movement of the stage, reference numeral 404 denotes a movement of the stopping stage, and reference numeral 405 denotes a stop of the stage 114.

Generally, the stage moves quickly to a destination and as the stage comes closer to the destination, the stage moves slowly to stop at a right position. However, the embodiment of the present invention is changed such that the stage is controlled with a stable velocity during movement to operate the stage in synchronization with the cell frames. The relationship between the velocity and the time is shown in FIG. 4.

The stage 114 is operated with a ball screw and the like. Thus generally, there is play in a gear and the backlash period 401 is provided during which the stage is not moved. After the period 401, the stage enters the initial acceleration period 402 for obtaining a fixed velocity, and then the stage enters the desired and stable stage movement period 403. After that, the stage enters the stage movement period 404 from when a stop command is issued to when the stage is actually stopped, and then the stage is stopped at 405.

Since the duration of the backlash period 401 depends upon a state of the gear when the stage is stopped immediately before the period 401, the necessary duration of the period 401 cannot be specified. Further, the durations of the initial movement period 402 of the stage 114 and the stage movement period 404 during which the stage is about to stop depend upon the moving velocity stabilized according to the magnification of the screen in the stage movement period 403 and the communication performance between the control computer 116 and the operation mechanism of the stage 114. This communication performance is determined by contention and the like with other communications.

As described above, the movement of the stage 114 is a complicated operation. When this operation is repeated for each screen, a number of moving errors are generated and the stopping accuracy exceeds the spacing between the cells, resulting in erroneous recognition. Although it is preferable to move the cell counting frames in synchronization with the stage movement including such an error, such a movement is difficult in practical use.

Thus in the embodiment of the present invention, the stage 114 is not stopped until reaching a destination of cell counting, and the cells are counted using the stable movement period 403 as much as possible according to the stage moving velocity of FIG. 4. In other words, instead of stopping the stage for each screen, the stage is not stopped until reaching the destination, an image of the stage is obtained during the movement, the image is compared with a desired image position and is corrected by shifting the image or displaying cell frames, and then cells are counted.

At the start of cell counting, the direction of movement of the stage 114 is first determined.

Figure 7:
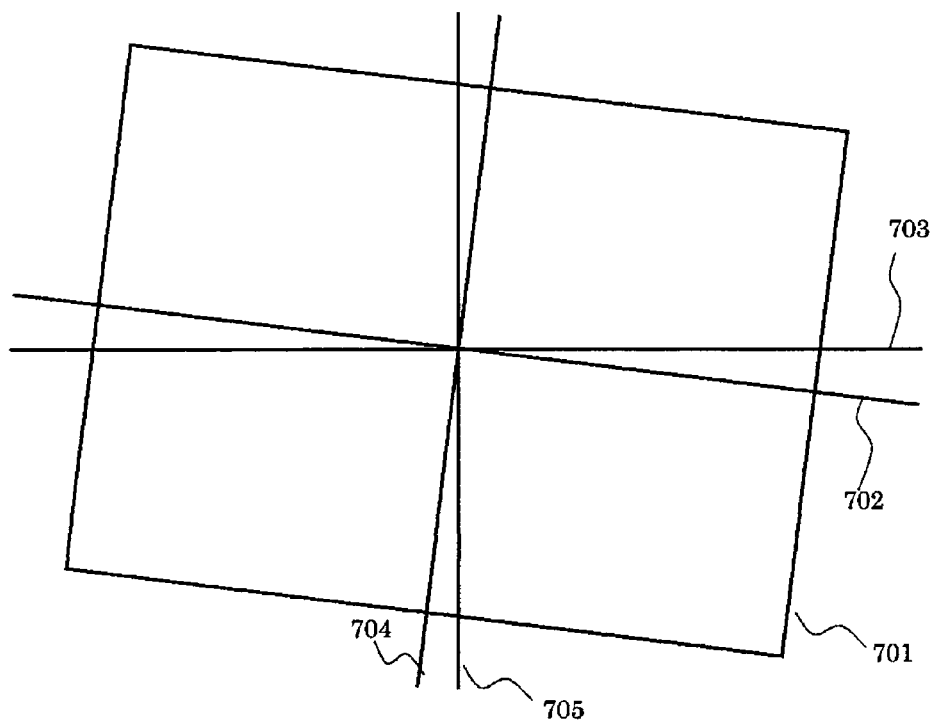
FIG. 7 is an explanatory drawing showing the stage and the rotation axis of an SEM.
Figure 8:
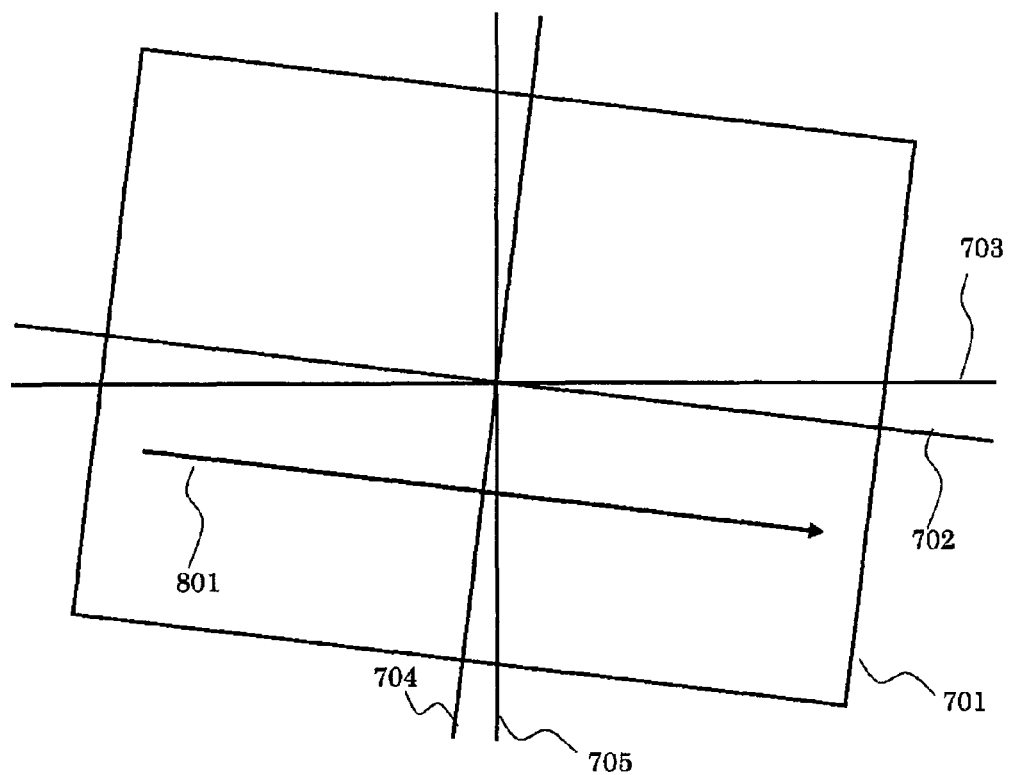
FIG. 8 is an explanatory drawing showing the processing of a raster rotation.
Figure 9:
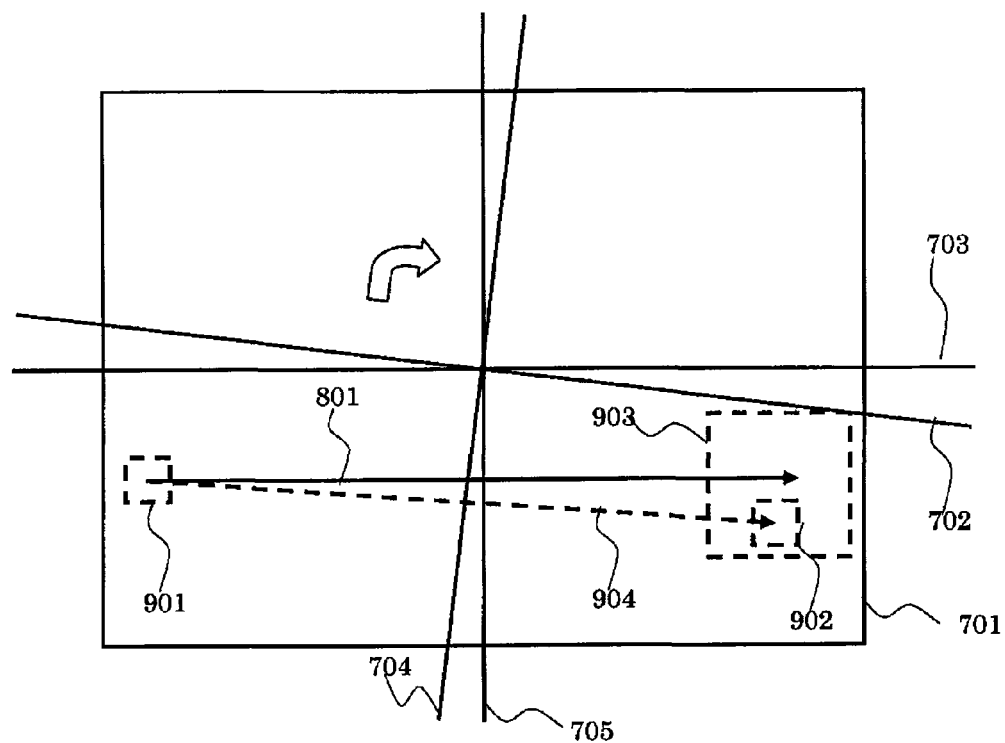
FIG. 9 shows a correction of the raster rotation.

The direction of cell counting and the direction of movement of the stage are determined. The detail of these directions is shown in FIGS. 7 to 9 (will be described later).

Even when the cells 201 seemingly move in the lateral direction, the stage 114 does not always move in the lateral direction. Regarding the direction of movement, the X-axis has three positive, 0, and negative directions and the Y-axis also has three positive, 0, and negative directions.

After that, backlash removing processing is performed. When the determined direction of movement is positive or negative, operations are performed along the X-axis and the Y-axis according to a backlash removing processing flow shown in FIG. 10.

Figure 10:
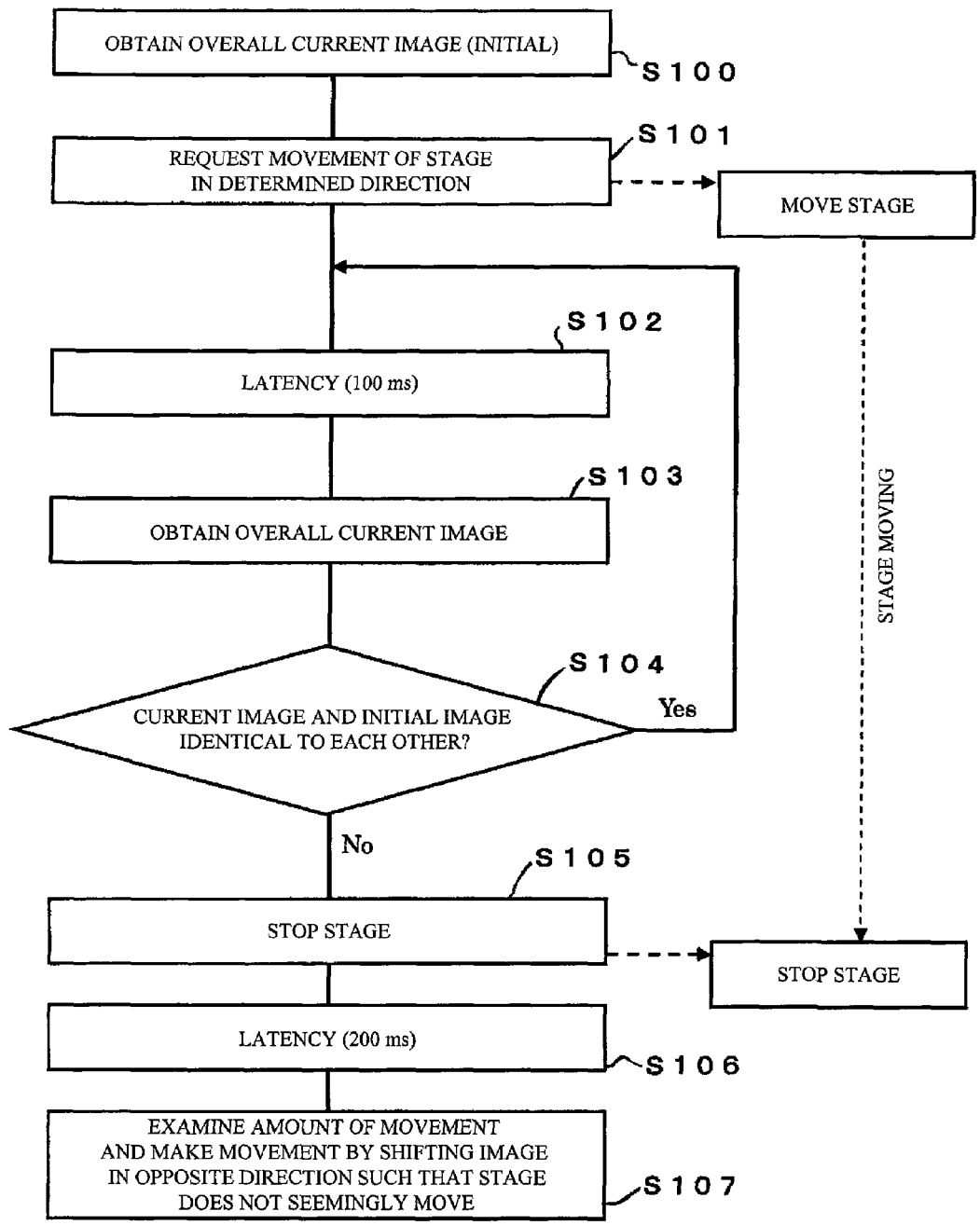
FIG. 10 is a flowchart showing the processing of removal of backlash.

In other words, in FIG. 10, the control computer 116 obtains the overall current image, a movement of the stage in the determined direction is requested, and then the stage starts moving (steps S100 and S101). After a predetermined latency time (e.g., 100 ms), the overall current image is obtained (steps S102 and S103). At this moment, it is important that the amount of movement during the latency time is smaller than a spacing between cells.

Next, in step S104, it is decided whether or not the current image and the initial image are identical to each other. When the images are identical to each other, the process returns to step S102. In step S104, when it is decided that the current image and the initial image are not identical to each other, the stage is stopped (step S105).

Next, after a latency time (e.g., 200 ms), the amount of movement is examined based on a fact that the maximum movement is not larger than a half of the cell. A movement to the closest cell is made by shifting the image and thus seemingly, the stage does not move (step S107).

The latency time of FIG. 10 varies depending upon the performance of the CPU of the control computer 116 and the moving velocity of the stage 114.

The image is obtained over the screen (steps S100 and S103) because it is not possible to decide whether the image is characteristic or not. For this reason, images on the overall largest screens are compared with each other, causing a demerit of performance degradation. Thus when problems occur in performance, the size of an image is reduced. Further, backlash is removed twice along the X-axis and the Y-axis.

Next, processing during the initial movement is performed.

During the initial movement, a delay time occurs from when the computer 116 requests communications to when the stage 114 actually moves and an image becomes viewable. The latency time is provided to compensate for the delay time and the low initial velocity of the stage 114.

Next, processing during a stable stage movement is performed. In other words, the velocity of the stage is determined by the magnification of the screen.

Figure 11:
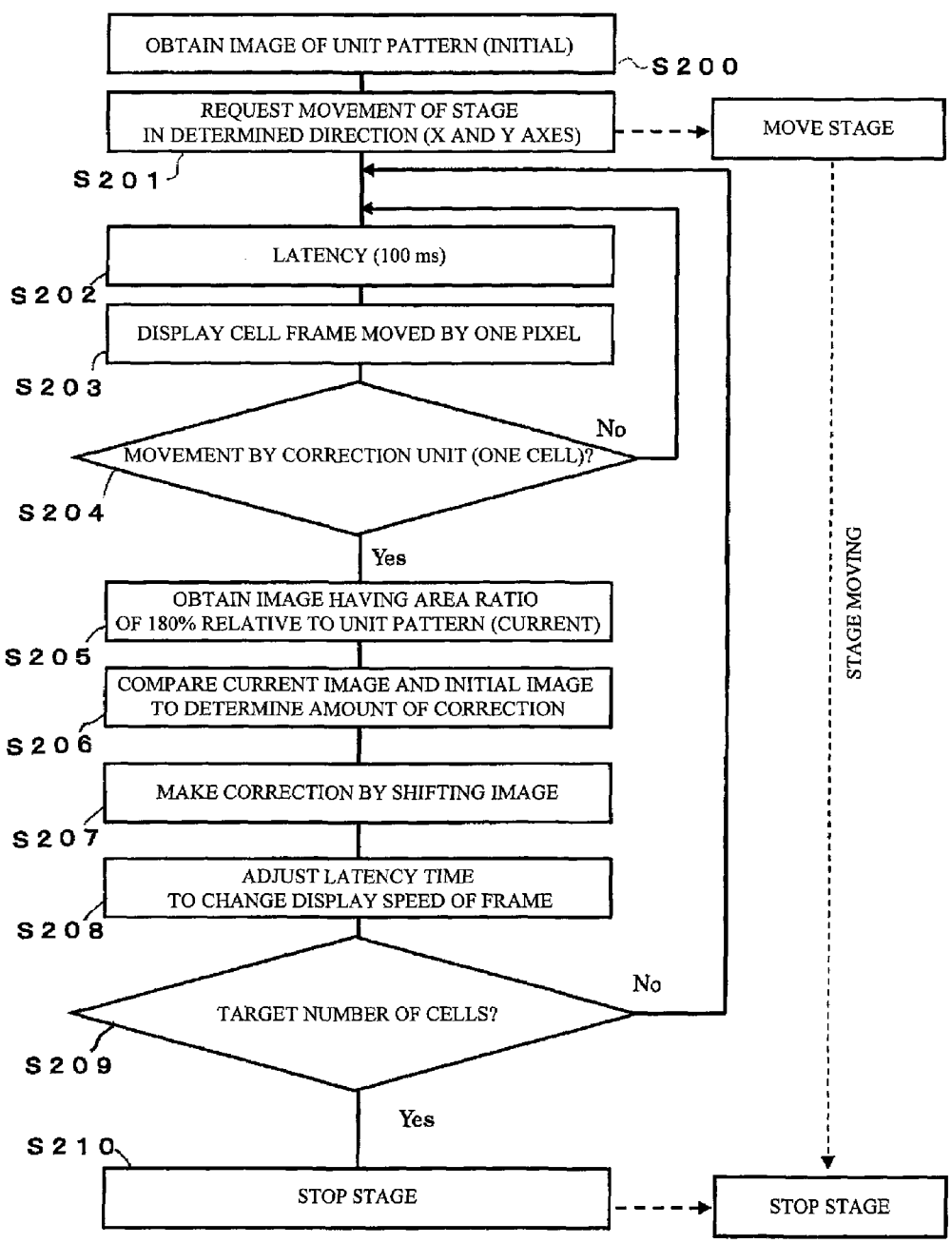
FIG. 11 is a flow chart showing the processing of cell counting.

A processing flow of cell counting is implemented according to FIG. 11.

In other words, in FIG. 11, an image of a unit pattern is obtained, a movement of the stage 114 in the determined direction is requested, and the stage starts moving (steps S200 and S201). After a predetermined latency time (e.g., 100 ms), cell frames moved by one pixel are displayed (steps S202 and S203).

Next, in step S204, it is decided whether or not the stage has been moved by a correction unit (one cell). When the image has not been moved by the correction unit, the process returns to step S202. In step S204, when it is decided that the stage has been moved by the correction unit (one cell), an image having an area ratio of 180% relative to the unit pattern is obtained and the current image and the initial image are compared with each other to calculate an amount of correction of movement (steps S205 and S206).

After that, the image is shifted and corrected by using the calculated amount of correction, and the latency time is adjusted to change the display speed of the frame (step S208). This operation is counted as one cell and it is decided whether or not the number of counts is a target number of cells (step S209).

When the number of counts is not the target number of cells, the process returns to step S202.

When the number of counts reaches the target number of cells in step S209, the movement of the stage 114 is stopped.

The latency time of FIG. 11 varies depending upon the performance of the CPU of the control computer 116 and the moving velocity of the stage. The area ratio of FIG. 11 varies depending upon the size of the unit pattern and image recognition. Further, the correction unit varies depending upon the spacing between the cells, the size of the unit pattern, and image recognition. Moreover, regarding the amount of movement of the screen, the number of moving pixels varies depending upon the moving velocity of the cell frame and the magnification of the screen. Since the velocity of the stage cannot be changed, the timing of displaying the cell frames is changed to adjust the velocity.

The following is a correction in the processing of the stable stage movement.

Figure 5:
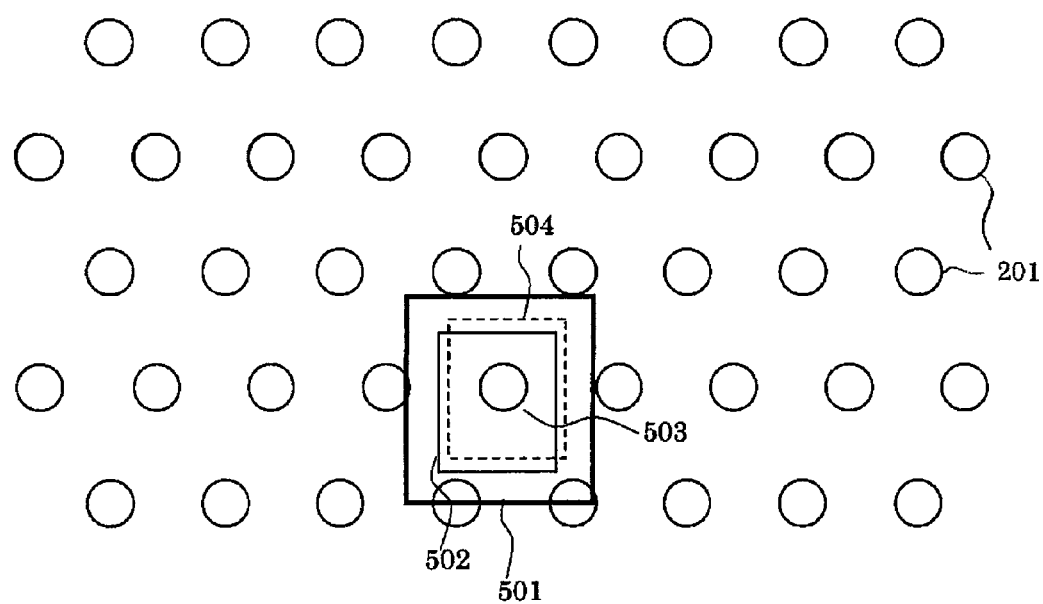
FIG. 5 is an explanatory drawing showing a method of internal correction for a movement corresponding to about one cell.

FIG. 5 is an explanatory drawing showing a method of internal correction for a movement corresponding to about one cell. In FIG. 5, reference numeral 501 denotes a cell area including an error of the movement of the stage 114, reference numeral 502 denotes a position on which a cell should be disposed according to calculations, reference numeral 503 denotes a cell to be confirmed, and reference numeral 504 denotes an actual position of the moved cell.

In the present invention, although the cell area is used as a correction area, the same area should not be always used. When the cell area is different from the correction area, it is necessary to set another correction confirmation area but a concept regarding a correction is the same. For example, when a spacing between the cells is not the unique minimum unit or when an area unique to the cell area is so small that a hit rate is within an error range, the cell area which is the same as the correction area does not enable a decision on the same image. Thus another correction area is provided in the cell area.

In FIG. 5, an image having a rectangular frame of a unit pattern is obtained before cell counting. When the stage is move by one cell to the right, an image of the cell area 501 including an error of the movement of the stage is obtained during the movement of the stage. In the cell area 501 including the error of movement, pattern matching to the image having the rectangular frame of the unit pattern is performed, an amount of correction is determined based on the position on which the cell should be disposed and an actual position, and a relative amount is corrected by shifting the image because the stage is being moved.

When a cell is present outside the cell area 501 including the error of movement of the stage, the adjacent cell is erroneously recognized. Further, since the stage is being moved, the obtained image may not be correct. When the image cannot be recognized, the cell frame is entirely indicated by a broken line and the user is notified that the cell cannot be recognized. Thus whether or not cells are correctly counted can be decided by the human eye.

Further, an image shift knob is provided to stop a correction and the image shift knob can be manually corrected during cell counting, so that cells can be correctly counted.

Next, the stage is stopped.

Broadly speaking, the stage is stopped in two patterns.

In a first processing method, a movement to a stop position is confirmed, the stage is stopped, an image is recognized after a latency time equivalent to the stopping operation, and a cell frame is displayed to be aligned with the current position of the cell. In this case, the drawback is the end position advancing too much relative to the start position of cell counting.

In a second processing method, the stage is stopped at the final half of a cell and is moved by shifting an image from a stop position to the position of an end point. In this case, although the start position and the end position are aligned, an amount of the image shift is large because the image is shifted.

The first and second stopping methods can be selected by the user, so that cells can be counted in a desired manner.

Figure 6:
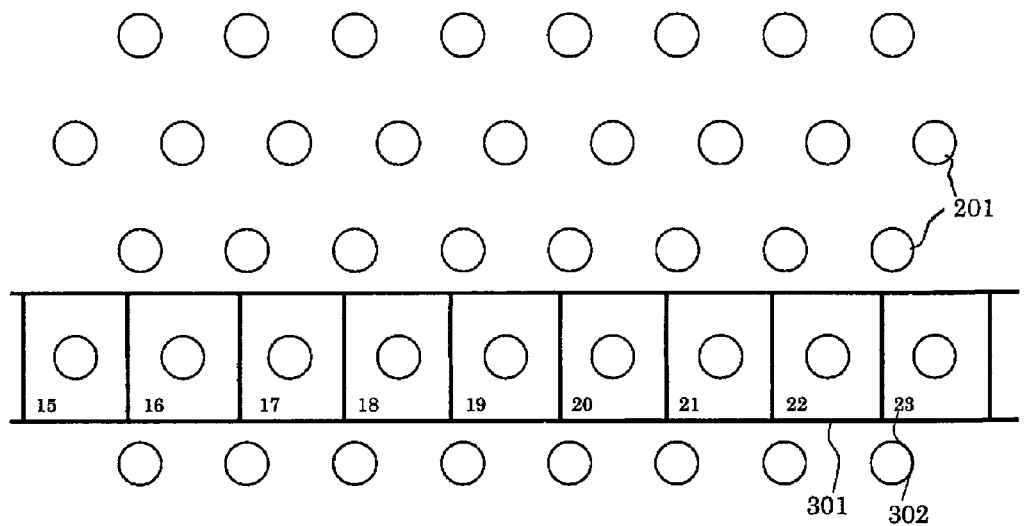
FIG. 6 shows a screen during a movement for cell counting.

FIG. 6 shows a screen during a movement for cell counting. The counter number 302 increases with the movement of the stage.

Originally, during the image shift, a field of view is moved by moving an electron beam without moving the stage. For example, in a typical image shifting method, an SEM having probes brings one of the probes into contact with a position away from another probe that is brought into contact with a sample. Thus when the stage is moved, the probe in contact with the stage is broken. For this reason, the stage cannot be moved.

However, by shifting an image, it is possible to observe another position with the SEM without moving the stage and bring another probe into contact with a sample.

In the embodiment of the present invention, an image is slightly shifted many times as if the stage operated, and the image is displayed so as to overlay a cell counter. Thus individual cells can be correctly counted. In this case, a cell frame is moved by a fixed distance and learning correction is performed to correctly include an amount of image shift in the cell frame, so that a cell can be smoothly displayed in the cell frame. Further, by shifting an image by a half cell frame, a single cell frame, and multiple cell frames and correcting the image by image recognition, the image can be quickly moved.

The operating range of the image shift is several tens to 200 μm angle or less, which is smaller than the operating range of the movement of the stage. However, the image shift causes no errors when the stage is stopped, thereby achieving cell counting with higher quality. The operating range of 200 μm angle or less is considered to mostly enable a movement to a destination. Cell counting using the image shift has two drawbacks as follows:

The first drawback is that a large image shift amount is necessary for reaching a destination.

The second drawback is that in the case of an SEM and the like having probes, the probe is placed on the origin of the image shift and the invisible probe has to be moved to a destination.

In order to remove the two drawbacks, in counting using the image shift, offset processing is provided for the stage and the image shift. In this processing, the stage 114 is moved in the opposite direction from the image shift and an image on the screen is not changed while an amount of the image shift is returned to the origin. Further, the image moving in the same direction can quickly move with a small amount of image shift. At this moment, the amount of image shift can be also set such that the sum of the amount of movement of the stage and the amount of image shift is a fixed amount of movement. Thus cells can be quickly counted in a stable manner with a small amount of image shift.

Figure 13:
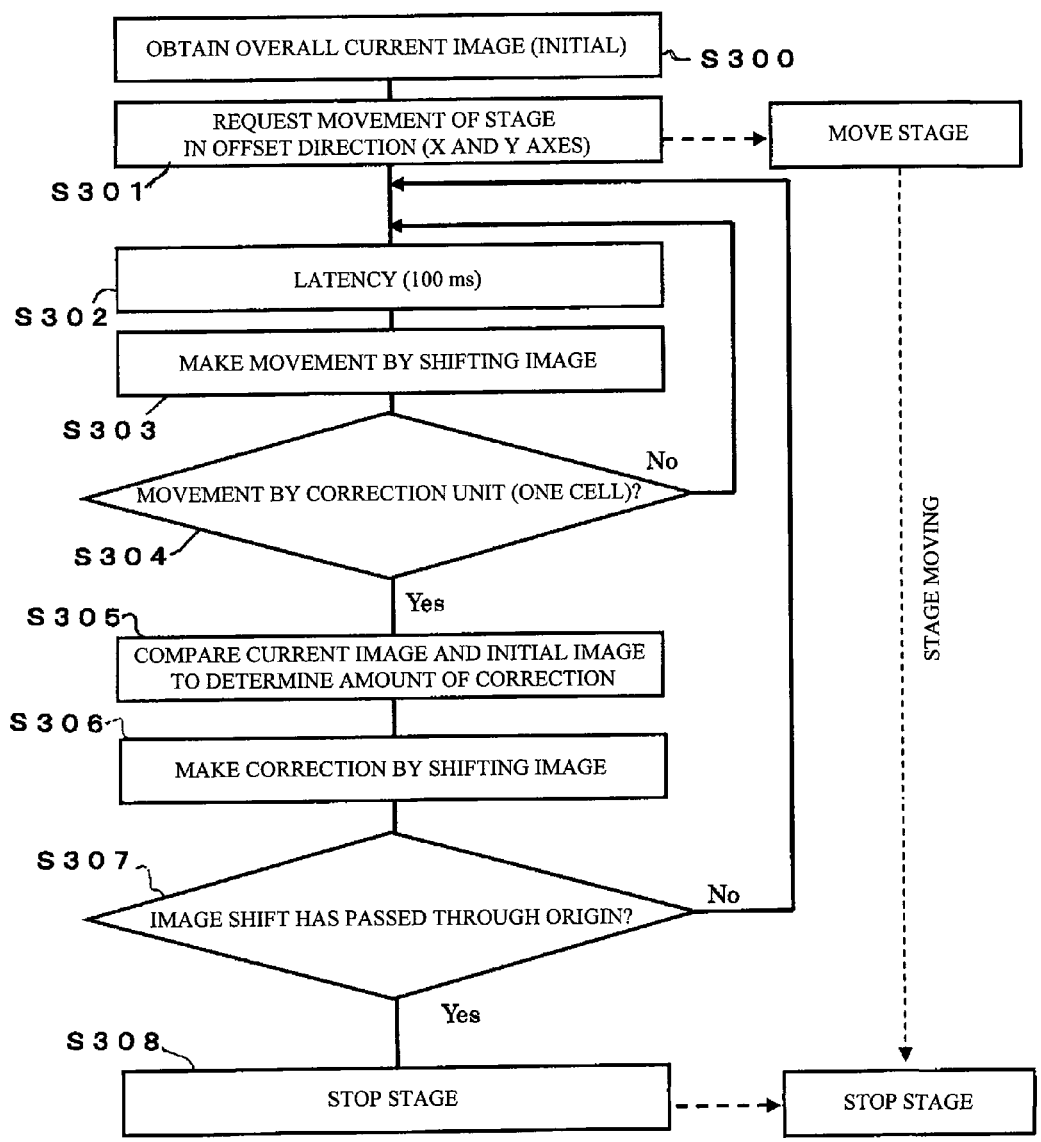
FIG. 13 is a flowchart of offset processing.

FIG. 13 shows a flow of the offset processing. In FIG. 13, the overall current image (initial image) is obtained, a movement of the stage 114 in an offset direction is requested, and the stage starts moving (steps S300 and S301). After a predetermined latency time (e.g., 100 ms), the image is moved by the image shift (steps S302 and S303).

Next, in step S304, it is decided whether or not the stage has been moved by a correction unit (one cell). When the image is not moved by the correction unit, the process returns to step S302. In step S304, when it is decided that the stage has been moved by the correction unit (one cell), the current image and the initial image are compared with each other to calculate an amount of correction of movement, and the movement of the image is corrected by the image shift (steps S305 and S306).

After that, the latency time is adjusted and it is decided whether or not the image shift has passed through the origin (step S307). In step S307, when it is decided that the image shift has not passed through the origin, the process returns to step S302. On the other hand, in step S307, when it is decided that the image shift has passed through the origin, the movement of the stage 114 is stopped (step S308).

Since the stage 114 operates during the offset processing, removal of backlash and termination are naturally necessary. These operations are performed in a similar manner to the foregoing operations and thus are omitted in FIG. 13.

The offset processing flow is similar to the foregoing flow of removing backlash and the foregoing flow of counting cells, and thus the offset processing flow is easy to produce. Even out of the range of the image shift, offset processing and a plurality of times of cell counting by the image shift make it possible to reach a destination, improving usability.

After the stage is stopped as shown in FIG. 13, pattern recognition is performed again to make the final correction. Although a slight shift occurs from the origin of the image shift, the screen can be correctly returned to the original position. Further, by performing the offset processing immediately after cells are counted by moving the stage, a movement of the image shift used for the correction can be returned to the origin, thereby improving usability.

The above explanation described a variety of corrections made by image recognition. When an image color is changed by contamination and the like, a cell may not be recognized. This problem can be solved by comparing images after binarizing the images and performing edge enhancement.

However, it should be noted that unlike an edit of ordinary static images, the delay of the display of cell frames may cause a problem unless the processing is completed in a short time, for example, during the movement of the stage. It is important to edit images with the minimum processing. In order to increase performance, it is preferable to edit the minimum area on memory. Further, an image is enlarged during an edit of the image to have a higher magnification than an actual magnification, thereby preventing a concentration of electron beams. Thus it is also effective to perform the processing in environments where contamination hardly occurs.

Next, a raster rotation is set to move the stage with higher accuracy.

In this process, the work distance, the display magnification, the stigma, the aperture alignment, the beam position of an optical system are set, and the raster rotation is set as below to reduce an error of the movement of the stage. After that, cells are counted as described above.

Figure 12:
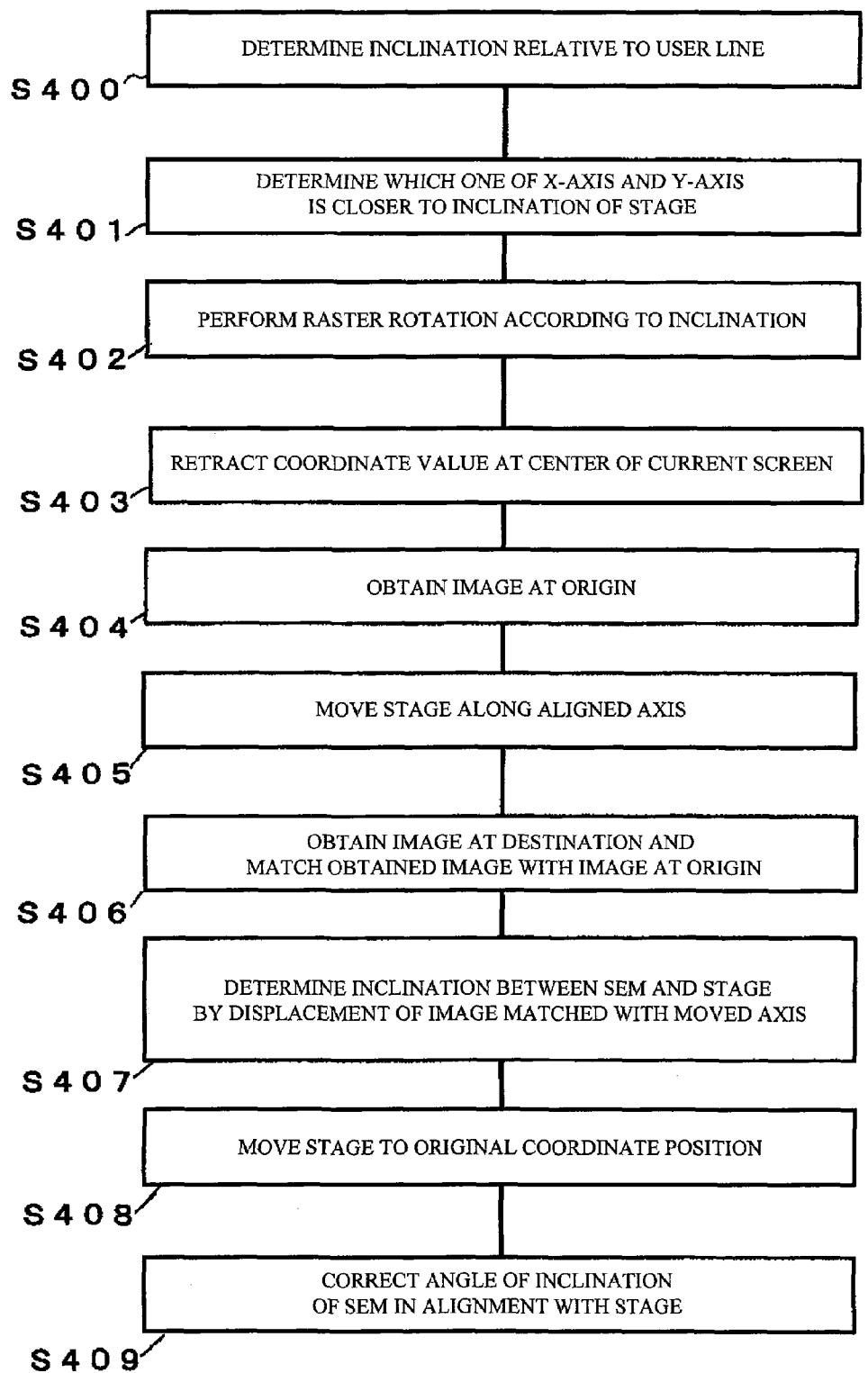
FIG. 12 is a flow chart showing the processing of the raster rotation.

FIG. 12 is a flowchart showing the steps of setting the raster rotation.

In FIG. 12, the inclination of the stage is determined relative to a line designated by the user, which one of the X-axis and the Y-axis is closer to the inclination is determined, and the raster rotation is performed according to the determined inclination (steps S400, S401, and S402).

Next, a coordinate value at the center of the current screen is stored (retracted) in storage means, the image at the origin is obtained, and the stage 114 is moved along the aligned axis (steps S403, S404 and S405).

And then, an image at a destination is obtained, matched with the image at the origin, and an inclination between the SEM and the stage 114 is determined by the displacement of the image (steps S406 and S407). Thereafter, the stage 114 is moved to the original coordinate position, and the angle of inclination of the SEM is corrected to be aligned with the stage 114 (steps S408 and S409).

Generally, a deviation of several degrees occurs when a sample is placed on the sample pedestal. The function of the raster rotation to correct this deviation is publicly known. However, a deviation between the axis of the optical system and the rotation axis of the stage in each measurement environment is not taken into consideration. This method will be described below.

FIG. 7 shows the stage 114 and the rotation axis of the SEM. Reference numeral 701 denotes the overall stage 114, reference numeral 702 denotes the X-axis of the stage 114, reference numeral 703 denotes the X-axis of the SEM, reference numeral 704 denotes the Y-axis of the stage 114, and reference numeral 705 denotes the Y-axis of the SEM.

In FIG. 7, the rotation axes of the stage 114 and the SEM are deviated from each other, so that the stage 114 is seemingly inclined. Although the sample and the stage 114 may be originally deviated from each other in terms of angle, it is assumed that the angles of the sample and the stage 114 are equal to each other in the following example in order to avoid a complicated explanation.

In order to match the inclination of the sample, the raster rotation is performed as shown in FIG. 8. In FIG. 8, reference numeral 801 denotes an inclination of the sample. The inclination is designated by the user and can be determined by clicking the starting point of a vector 801 with the mouse and dragging the mouse to the arrow point of the vector 801 of a unit pattern.

The angle is determined by performing $\tan^{-1}$ based on the coordinate values of the starting point and the end point and the overall stage 114 is rotated by the determined angle, so that the sample or the stage 114 can be horizontally and vertically aligned with the SEM.

As shown in FIGS. 7 and 8, when the rotation axes of the stage 114 and the optical system are deviated from each other, the rotation axis of the stage 114 is also deviated by the angle determined by performing $\tan^{-1}$ based on the coordinate values of the starting and end points designated by the user. The setting of the raster rotation is publicly known.

FIG. 9 is an explanatory drawing showing that after the angle is seemingly adjusted, the stage 114 is moved in the direction of the arrow of the inclination 801 designated by the user. Reference numeral 901 denotes an image area at the origin, reference numeral 902 denotes an image at a destination, reference numeral 903 denotes a possible image area at the destination, and reference numeral 904 denotes an actual direction of movement of the stage.

The image 901 at the origin is obtained and stored in the memory before the movement, and then the stage 114 is moved.

Originally, the stage 114 should be horizontally moved because the raster rotation has been adjusted. However, the axis of the stage 114 is not horizontally aligned and thus the stage 114 is moved along the axis of the stage 114. After the movement, the possible image 903 at the destination is obtained and stored in the memory.

In the possible image area 903 at the destination, the image area 902 at the destination is found by matching for locating the image of the image area 901 at the origin. The optical system is horizontally aligned but the stage 114 is not horizontally aligned, causing such a deviation between the rotation axes. The angle of the deviation between the rotation axes can be determined by a difference between a level and a direction determined by the central points of the image area 901 at the origin and the image area 902 at the destination.

By changing the inclination of the optical system so as to rotate only the axis of the stage 114 by the angle of the deviation of the rotation axis, the optical axes of the optical system and the stage 114 can be aligned with each other.

The setting of the raster rotation is performed before cells are counted, so that even when the stage 114 is move during cell counting, an error caused by a difference between the rotation axes of the optical system and the stage 114 is eliminated and the cell is more accurately placed in the cell frame. Thus cells can be counted with higher accuracy.

The rotation axis of the optical system changes with the focal length of the electron gun 106, and thus a deviation from the rotation axis of the stage 114 varies in each observation. However, in the conventional art, the rotation axis of the optical system is aligned only based on a basic focal length and the conventional art does not respond to a change in the focal length of the electron gun 106, so that an error is caused by a deviation between the rotation axis of the optical system and the axis of the stage 114.

With the setting of the raster rotation according to the embodiment of the present invention, a deviation from the axis of the stage can be eliminated with a simple operation in each observation environment, thereby improving operability.

As described above, the present invention makes it possible to achieve a semiconductor testing method, a semiconductor tester, and an operation program in the semiconductor tester by which semiconductor cells can be quickly counted with accuracy.

Some SEM apparatuses can rotate samples. Such an SEM apparatus can originally rotate the stage 114 and a sample into alignment with an SEM, thereby eliminating the need for processing of raster rotation.

Further, cells can be counted while being moved in one of the X-axis direction and the Y-axis direction, achieving high accuracy.

The foregoing embodiment is merely an example of the present invention and the present invention is not limited to this embodiment.

What is claimed is:

1. A semiconductor testing method in which a plurality of cells formed in a semiconductor are displayed on display means based on a sample signal obtained by irradiating the semiconductor on a movable stage with a charged particle beam, and a specific cell is identified, the method comprising the steps of:

displaying a rectangular frame surrounding each of the cells displayed on the display means and formed in the semiconductor, and displaying a numeric value corresponding to the cell in the displayed rectangular frame;

displaying the rectangular frame and the numeric value and simultaneously moving the stage to move the semiconductor based on the sample signal obtained from the semiconductor; and correcting an amount of error caused by image recognition when the stage moves at a fixed velocity, counting the cells, and identifying the specific cell while confirming the numeric value corresponding to the cell.

2. The semiconductor testing method according to claim 1, wherein the stage has a fixed amount of velocity relative to an X-axis and a Y-axis intersecting each other, and the stage is moved in a fixed movement vector direction.

3. The semiconductor testing method according to claim 1, wherein offset processing for a movement of the stage and image shift and removal of backlash are performed in a state in which a display screen of the display means is static.

4. The semiconductor testing method according to claim 1, wherein the amount of error is corrected after edge enhancement, binarization, and enlargement are performed on a semiconductor image displayed on the display means.

5. The semiconductor testing method according to claim 1, wherein the semiconductor on the stage is irradiated with the charged particle beam by using an electron microscope, and a deviation between an axis of the electron microscope and a rotation axis of the stage is corrected in each test condition.

6. The semiconductor testing method according to claim 1, wherein the numeric value corresponding to the displayed cell is changeable.

7. A semiconductor tester comprising a movable stage for supporting a semiconductor, a charged particle beam irradiation optical system for irradiating the semiconductor on the stage with a charged particle beam, a monitor for displaying, based on a sample signal obtained by irradiating the semiconductor with the charged particle beam, a plurality of cells formed in the semiconductor, and a control unit for controlling the stage, the charged particle beam irradiation optical system, and the monitor, the semiconductor tester identifying a specific cell, wherein the control unit displays a frame surrounding each of the cells displayed on the monitor and formed in the semiconductor, and displays a numeric value corresponding to each of the cell, and wherein the control unit count cells, while moving the semiconductor, following a movement of the cells displayed on the monitor, and displays the frame and the numeric value in synchronization with the movement of the cells to identify the specific cell.

8. The semiconductor tester according to claim 7, wherein the control unit is configured to move the stage with a fixed amount of velocity relative to an X-axis and a Y-axis intersecting each other and to move the stage in a fixed movement vector direction.

9. The semiconductor tester according to claim 7, wherein the control unit is configured to perform offset processing for the movement of the stage and the image shift and removal of backlash in a state in which a display screen of the monitor is static.

10. The semiconductor tester according to claim 7, wherein the control unit is configured to correct an amount of error after performing edge enhancement, binarization, and enlargement on a semiconductor image displayed on the monitor.

11. The semiconductor tester according to claim 7, wherein the semiconductor on the stage is irradiated with the charged particle beam by using an electron microscope, and the control unit corrects a deviation between an axis of the electron microscope and a rotation axis of the stage in each test condition.

12. The semiconductor tester according to claim 7, wherein the control unit is configured to change the numeric value corresponding to the displayed cell.

13. A computer program on a machine-readable medium for making a computer function to control a semiconductor tester comprising a movable stage for supporting a semiconductor, charged particle beam irradiation means for irradiating the semiconductor on the stage with a charged particle beam, display means for displaying, based on a sample signal obtained by irradiating the semiconductor with the charged particle beam, a plurality of cells formed in the semiconductor, and control means for controlling the stage, the charged particle beam irradiation means, and the display means, the semiconductor tester identifying a specific cell, wherein the program is configured to:

display a rectangular frame to surround each of the cells displayed on the display means and formed in the semiconductor, and display a numeric value corresponding to the cell in the displayed rectangular frame;

control the stage to move the semiconductor, while the rectangular frame and the numeric value are displayed, based on the sample signal obtained from the semiconductor; and correct an amount of error, count the cells, and identify the specific cell while the numeric value corresponding to the cell is confirmed.

14. A semiconductor testing method in which a plurality of cells formed in a semiconductor are displayed on a display based on a sample signal obtained by irradiating the semiconductor on a movable stage with a charged particle beam, and a specific cell is identified, the method comprising the steps of:

displaying a frame surrounding each of the cells displayed on the display and formed in the semiconductor, and displaying a numeric value corresponding to the cell in the displayed frame; and counting cells, while moving the semiconductor, following a movement of the cells displayed on the monitor, and displaying the rectangular frame and the numeric value in synchronization with the movement of the cells to identify the specific cell.

15. The semiconductor testing method according to claim 14, wherein the stage has a fixed amount of velocity relative an X-axis and a Y-axis intersecting each other, and the stage is moved in a fixed movement vector direction.

16. The semiconductor testing method according to claim 14, wherein offset processing for a movement of the stage and image shift and removal of backlash are performed in a state in which a display screen of the display means is static.

17. The semiconductor testing method according to claim 14, wherein the amount of error is corrected after edge enhancement, binarization, and enlargement are performed on a semiconductor image displayed on the display means.

18. The semiconductor testing method according to claim 14, wherein the semiconductor on the stage is irradiated with the charged particle beam by using an electron microscope, and a deviation between an axis of the electron microscope and a rotating axis of the stage is corrected in each test condition.

19. The semiconductor testing method according to claim 14, wherein the numeric value corresponding to the displayed cell is changed.

* * * * *